United States Patent
Vardi et al.

(10) Patent No.: US 11,672,778 B2
(45) Date of Patent: Jun. 13, 2023

(54) SLOW RELEASE CANNABINOIDS AND PRODUCTS THEREOF

(71) Applicants: Amnon Vardi, Ram On (IL); Nimrod Vardi, Ram On (IL); Omer Vardi, Ram On (IL)

(72) Inventors: Amnon Vardi, Ram On (IL); Nimrod Vardi, Ram On (IL); Omer Vardi, Ram On (IL)

( * ) Notice: Subject to any disclaimer, the term of this patent is extended or adjusted under 35 U.S.C. 154(b) by 0 days.

(21) Appl. No.: 17/863,428

(22) Filed: Jul. 13, 2022

(65) Prior Publication Data
US 2022/0347154 A1  Nov. 3, 2022

Related U.S. Application Data

(63) Continuation of application No. 16/760,496, filed as application No. PCT/IL2019/051120 on Oct. 15, 2019, now abandoned.

(60) Provisional application No. 62/745,628, filed on Oct. 15, 2018.

(51) Int. Cl.
*A61K 31/352* (2006.01)
*A61K 9/70* (2006.01)
*A61K 31/05* (2006.01)
*A61K 47/32* (2006.01)

(52) U.S. Cl.
CPC .......... *A61K 31/352* (2013.01); *A61K 9/7084* (2013.01); *A61K 31/05* (2013.01); *A61K 47/32* (2013.01)

(58) Field of Classification Search
CPC .... A61K 31/05; A61K 9/7084; A61K 9/7069; A61K 9/0014; A61K 9/7053; A61K 31/192; A61K 31/352; A61K 47/32; A61K 2300/00
See application file for complete search history.

(56) References Cited

U.S. PATENT DOCUMENTS

| | | | |
|---|---|---|---|
| 5,776,481 A | 7/1998 | Karst | |
| 6,328,992 B1 * | 12/2001 | Brooke | A61K 9/7084 424/443 |
| 6,632,522 B1 * | 10/2003 | Hyde | C09J 133/06 524/505 |
| 6,682,757 B1 | 1/2004 | Wright | |

(Continued)

FOREIGN PATENT DOCUMENTS

| | | |
|---|---|---|
| EP | 0722656 | 7/1996 |
| EP | 3179856 | 6/2017 |

(Continued)

OTHER PUBLICATIONS

H.S. Katz, Handbook for Filler for Plastics, p. 198, published 1987.

*Primary Examiner* — Jianfeng Song
(74) *Attorney, Agent, or Firm* — JMB Davis Ben-David

(57) ABSTRACT

There is provided a plastic material comprising at least one cannabinoid embedded within a structural polymer, wherein the plastic material is formulated to exude the at least one cannabinoid through an outer surface of the plastic material at a therapeutically effective rate for a period of at least a week or at least a month. The plastic material may comprise a liquid-absorbent material embedded within the structural polymer and a carrier oil absorbed into the liquid-absorbent material, wherein at least one cannabinoid is dissolved in the carrier oil.

17 Claims, 2 Drawing Sheets

(56) References Cited

U.S. PATENT DOCUMENTS

| | | | |
|---|---|---|---|
| 11,247,032 B1* | 2/2022 | Knas | A61M 35/10 |
| 2015/0098983 A1 | 4/2015 | Pongpeerapat | |
| 2016/0338974 A1 | 11/2016 | Aung-Din | |
| 2018/0169033 A1* | 6/2018 | Aoyagi | A61K 31/138 |
| 2018/0344676 A1* | 12/2018 | Hoag | A61K 36/185 |

FOREIGN PATENT DOCUMENTS

| | | |
|---|---|---|
| FR | 2901132 | 11/2007 |
| WO | 2013006729 | 1/2013 |
| WO | 2015161165 | 10/2015 |

* cited by examiner

SLOW RELEASE CANNABINOIDS AND PRODUCTS THEREOF

RELATED APPLICATIONS

This is a Continuation of U.S. patent application Ser. No. 16/760,496, filed Apr. 30, 2020, which is the US National Stage of International Patent Application No. PCT/IL2019/051120, filed Oct. 15, 2019, which in turn claims the benefit of U.S. Provisional Application 62/745,628 filed Oct. 15, 2018. The contents of the foregoing patent applications are incorporated by reference herein in their entirety.

BACKGROUND

Cannabidiol (CBD) is one of several cannabinoids found naturally in the *cannabis* plant. Over 100 different cannabinoids have been identified in *cannabis* plants such as *Cannabis sativa, Cannabis indica*, and *Cannabis ruderalis*. In addition to CBD, other cannabinoids include the primary psychoactive component of the *Cannabis* plant, tetrahydrocannabinol (THC), cannabinol (CBN), and Cannabigerol (CBG).

Whilst THC is a known psychoactive drug, CBD is devoid of psychoactive activity and has analgesic, anti-inflammatory, antineoplastic and chemo-preventive properties. Upon administration, CBD can exert its anti-proliferative, anti-angiogenic and pro-apoptotic activity through a variety of different mechanisms and works in a different way to THC in that it does not bind cannabinoid receptors directly. CBD has also been shown to be effective in the treatment of Multiple Sclerosis and childhood epilepsy. Although CBD constitutes up to 40 percent of the extract of the *Cannabis sativa* plant, due to its multiple medical benefits coupled with the fact that it is non-psychoactive, new strands of *cannabis* are being developed wherein the yield of CBD in the concentrated extract approaches 70% by weight and higher. CBD has a boiling point of 463 degrees Celsius and is known to be heat-stable and less prone to oxidation compared to THC.

Cannabinoids can be introduced into the body in multiple different ways including inhalation of *cannabis* smoke or vapor, aerosol sprays into the cheek, and by ingestion. It may be supplied as a concentrated oil, capsules, dried *cannabis*, or as a prescription liquid solution. However, taking cannabinoids orally has various drawbacks, for example, cannabinoids undergo substantial first-pass metabolism, wherein the gastric environment and liver metabolizes the cannabinoids so that their concentration is greatly reduced before it reaches the systemic circulation. In addition, oral administration of cannabinoids may be ineffective in patients who are experiencing nausea and vomiting as side effects from other medications. Another issue with oral administration, is that patients absorb the drug relatively rapidly and receive high drug concentrations in their body. These high drug concentrations, or peak levels, may be undesirable and limit the efficacy of the cannabinoids.

Transdermal delivery is another potential route for administration of cannabinoids as it circumvents the gastric system increasing bioavailability. The skin serves as an effective barrier to microbes and foreign molecules, however, small lipophilic molecules such as cannabinoids can diffuse across the skin. While creams and lotions may be used as a way of administering lipophilic agents, they have the drawback of being short-acting and may be accidentally rubbed or washed off the skin resulting in difficulty in achieving consistent or therapeutically effective levels of drug in the bloodstream. Therefore, a need exists for a method of transdermal delivery of cannabinoids over an extended period of time, by way of example, over a period of a week, a month, or up to several months.

SUMMARY

An aspect of the disclosure relates to solid compositions comprising a plastic material embedded with one or more cannabinoids, the plastic material being formulated for an extended release of the embedded cannabinoid.

For convenience of presentation, a plastic matrix containing a cannabinoid in accordance with an embodiment of the invention may be referred to herein as a plastic-cannabinoid matrix (PCM).

Throughout the specification, "extended release" refers to the release of an agent from a material and/or into the bloodstream of a subject over an extended period of time, by way of example about a week, about two weeks, about a month, or over a month. The term may be used interchangeably with "slow release" or "sustained release".

In an embodiment of the disclosure, the cannabinoid comprises one or a combination of two or more of CBD, a tetrahydrocannabinol (THC), a cannabichromene (CBC), a cannabigerol (CBG), and a cannabidivarin (CBDV). Optionally, the cannabinoid comprises or consists substantially of CBD.

In an embodiment of the disclosure, the PCM comprises a structural polymer comprising one or a combination of two or more of: a polyolefin such as a polyethylene (PE), a polyvinyl chloride (PVC), a thermoplastic polyurethane (TPU) and a synthetic-butadiene rubber (SBR).

An embodiment of the disclosure relates to a plastic cannabinoid wearable device (PCWD) comprising a PCM that is configured to release the one or more cannabinoids over an extended period of time of 1 week or more. In an embodiment of the disclosure, a PCWD comprises or consists of a PCM that is molded into a shape suitable for being worn by a subject, by way of example a necklace, a wristband, a bracelet or a shoe insert. In an embodiment of the disclosure, the PCWD is a non-adhesive device. Optionally, the PCWD is non-adhesive.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the disclosure are described below with reference to figures attached hereto that are listed following this paragraph. Identical features that appear in more than one figure are generally labeled with a same label in all the figures in which they appear. A label labeling an icon representing a given feature of an embodiment of the disclosure in a figure may be used to reference the given feature. Dimensions of features shown in the figures are chosen for convenience and clarity of presentation and are not necessarily shown to scale.

DETAILED DESCRIPTION

Figure 1:
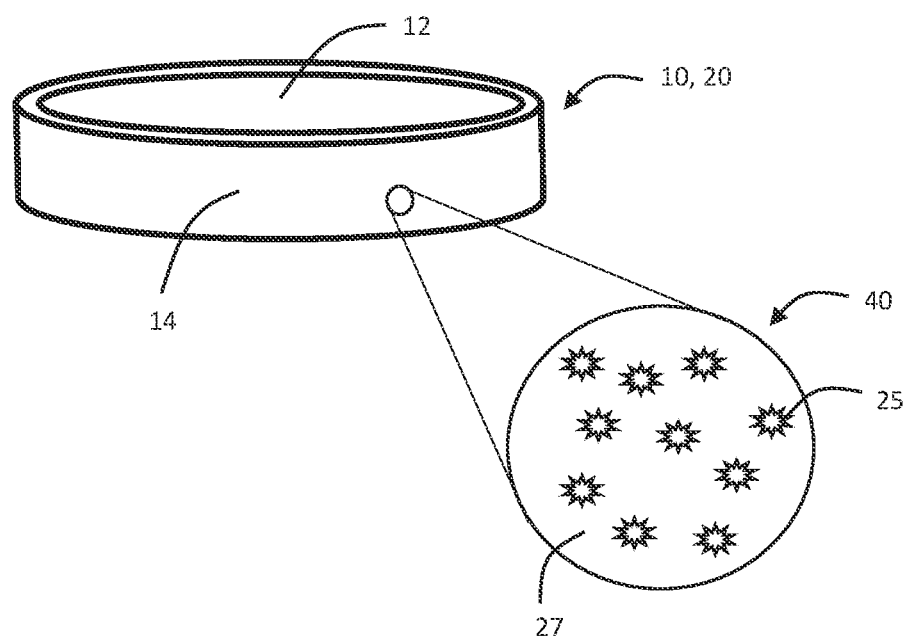
FIG. 1 schematically shows a wristband-shaped PCWD in accordance with an embodiment of the disclosure.
Figure 2:
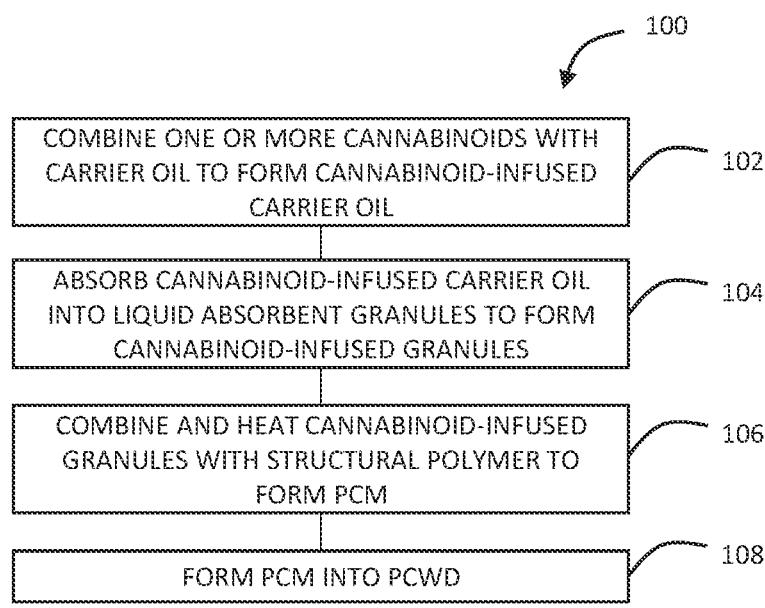
FIG. 2 shows a flowchart of a method of producing a PCWD in accordance with an embodiment of the disclosure.

An aspect of the disclosure relates to a providing a PCM comprising a structural polymer and one or more cannabinoids as an active ingredient embedded within the structural polymer, wherein the one or more cannabinoids are released through a surface of the PCM at a therapeutically effective rate for an extended period of time.

"Cannabinoids" as used herein refer to a diverse class of chemical compounds that act on cannabinoid receptors on cells and influence neurotransmitter release in brain. These receptor proteins include endocannabinoids produced naturally in humans and animals, phytocannabinoids produced in *cannabis* and some other plants, and chemically manufactured synthetic cannabinoids, which may or may not be chemically identical to endocannabinoids or phytocannabinoids. As used herein, a "phytocannabinoid" comprises cannabinoids that are naturally occurring and can be extracted from a plant source, as well as synthetically manufactured compounds that are chemically identical to those cannabinoids that can be extracted from a plant source. An example of a phytocannabinoid includes Δ9-tetrahydrocannabinol (THC), which is the primary psychoactive compound of *cannabis*. Another example of a phytocannabinoid is CBD, which in some strains of *cannabis* comprises up to 40% of extracted plant resin. Different phytocannabinoids isolated from *cannabis* exhibit varied effects. Other examples of phytocannabinoids a cannabichromene (CBC), a cannabidivarin (CBDV), a cannabigerol (CBG) or combinations of cannabinoids with beneficial therapeutic properties. The cannabinoids as used herein may be provided in purified form, as part of a naturally occurring resin, or a *cannabis* derived extract that comprises the cannabinoids together with other *cannabis*-derived oils and/or resins. The term "cannabinoid" is not limited to the compound in its decarboxylated form, by way of example THC, but also includes cannabinoids in a precursor acid form, by way of example tetrahydrocannabinolic acid (THCA). Other examples of cannabinoids in precursor acid form includes cannabidiolic acid (CBDA), which is a precursor to CBD.

In an embodiment of the disclosure, the structural polymer comprises one or more of a flexible polymer or an elastomer with viscoelastic properties. The one or more polymers comprised in the structural polymer may be non-toxic and appropriate for extended periods of external contact on a skin of a human or animal subject. Optionally, the structural polymer comprises one or more selections from a group consisting of: a polyolefin such as a polyethylene (PE), a polyvinyl chloride (PVC), a polyurethane (PU), an ethylene vinyl acetate (EVA), and a synthetic rubber. The PE optionally comprises a low-density polyethylene (LDPE), a linear low-density polyethylene (LLDPE), or combinations thereof. The structural polymer may comprise polyurethane such as a thermoplastic polyurethane (TPU). Optionally, the synthetic rubber comprises a styrene-butadiene rubber, also known as a Poly(styrene-butadiene-styrene) rubber ("SBS rubber"), and/or a silicone rubber such as polysiloxane. In an embodiment of the disclosure, the structural polymer is formulated as an adhesive polymer or a non-adhesive polymer. In a more particular embodiment, the structural polymer may comprise PEs optionally selected from the group consisting of: a LLDPE, a LDPE, and a PE elastomer (by way of example one or more Dowlex™ resins). Optionally, the structural polymer comprises or consists of a LLDPE, a LDPE, and a PE elastomer.

In an embodiment of the disclosure, a PCM at least initially comprises one or more cannabinoids such that the cannabinoids is between 0.1% and 15% of the initial total weight of the PCM (% w/w), or between 0.5% w/w and 2.5% w/w of the initial total weight of the PCM.

In an embodiment of the disclosure, a PCM releases a cannabinoid at least at a given minimum release rate over a given duration. A duration during which the PCM releases cannabinoids at least at a given minimum rate may be referred to herein as an "effective release duration". Optionally, the effective release duration is about 1 week, about 2 weeks, about 4 weeks, about 2 months, about 4 months, or about 6 months. Preferably, the minimum release rate of cannabinoids from the PCM is a therapeutically effective rate for a subject. Optionally, the minimum release rate is between about 1 milligram per day (mg/day) and about 100 mg/day, about 1 mg/day, about 2 mg/day, about 5 mg/day, about 10 mg/day, about 25 mg/day, about 50 mg/day, about 100 mg/day, or about 200 mg/day. It will be appreciated that the cannabinoid content of a PCM will decrease as the cannabinoids get released, and a minimum initial amount of the cannabinoids comprised in a PCM can be calculated as at least the product of a desired minimum release rate and a desired effective release duration. By way of numerical example, for a PCM to have an effective release duration of 2 weeks, during which time the PCM releases cannabinoids at a minimum release rate of at least 10 mg/day, the PCM initially comprises at least 140 mg of cannabinoids (10 mg/day×14 days). By way of another numerical example, for a PCM to have an effective release duration of 1 month, during which time the PCM releases cannabinoids at minimum release rate of at least 50 mg/day, the PCM initially comprises at least 1.5 grams (g) of cannabinoids (50 mg/day×30 days). It would be understood that, in a case where the release rate of the cannabinoids decreases over time as total cannabinoid content of a PCM decreases, the initial cannabinoid content in the PCM would be even higher.

It may be desirable to formulate and/or configure a PCM to mitigate a reduction of cannabinoid release rate over the course of its effective release duration, in order to minimize a difference between an initial cannabinoid release rate and a minimum cannabinoid release rate of the PCM.

In an embodiment of the disclosure, a plastic comprised in a PCM is formulated to release cannabinoids at a desired release rate. Optionally, the PCM's release of the cannabinoids is not dependent on breakdown of the PCM, and the PCM remains substantially intact throughout the time of cannabinoid release. Optionally, release rate of a PCM is controlled by formulating a structural polymer to comprise a blend of different polymers so that structural polymer has a polarity within a desired range. Optionally, the desired range is a level of polarity that differs from the level of polarity of cannabinoids. Without being bound by theory, a structural polymer having a level of polarity similar to that of cannabinoids tends to retain the cannabinoids, and a structural polymer having a level of polarity different from that of cannabinoids tends to extrude the cannabinoids.

Optionally, a cannabnoid release rate of a PCM is controlled by embedding a liquid-absorbent material infused with a liquid cannabinoid composition into a structural polymer to form the PCM. The liquid cannabinoid composition may comprise one or more cannabinoids and a carrier oil. Optionally, and without being bound by theory, one or more cannabinoids comprised in the liquid cannabinoid composition diffuse out of the liquid-absorbent material into the structural polymer and is extruded out through an outer surface of the PCM, then transdermally passes into a subject's blood stream. Optionally, the one or more cannabinoids is thereby released in a therapeutically effective rate for at least one week, at least two weeks, or about a month or more. The extended release of the cannabinoids from the PCM advantageously allows the wearer of a PCWD comprising or shaped from the PCM to wear the device for extended periods of time and benefit from the extended cannabinoid release before requiring replacement.

Reference is made to FIG. 1, schematically showing a wristband-shaped PCWD 10 consisting of a PCM 20 in accordance with an embodiment of the disclosure. PCM 20 is formulated to comprise a structural polymer, one or more cannabinoids dissolved in a carrier oil comprising one or more non-volatile carrier oils; and granules 25 of a liquid-absorbent material infused with the cannabinoids and the carrier oil, with the granules 25 embedded within the structural polymer. The granules 25 are optionally provided in an amount sufficient to absorb the cannabinoids and the carrier oil prior to compounding with a structural polymer. The granules 25 are optionally embedded within the structural polymer in a substantially even distribution. Inset 40 schematically shows a magnified interior portion PCM 20 comprising liquid-absorbent granules 25 within the structural polymer 27.

The liquid-absorbent material, which may be in granular or particulate form, optionally comprises one or a combination of two or more selections from the group consisting of: a silica gel, a fumed silica (also known as pyrogenic silica), a carbon black, and an activated carbon. Silica gel is a porous silicon dioxide that is available in a wide variety of grain sizes. Fumed silica consists of microscopic droplets of amorphous silica fused into branched, chainlike, three-dimensional secondary particles which then agglomerate into tertiary particles having a high surface-to-volume ratio and typically having a size of about 5 nm to 50 nm. Activated carbon typically consists of charcoal that has been treated with either a combination of heat and pressure, or with strong acid or base followed by carbonization, to make it highly porous. Carbon black is a material produced by the incomplete combustion of heavy petroleum products, which is a form of paracrystalline carbon that has a high surface-area-to-volume ratio, but typically lower than that of activated carbon. Subtypes of carbon black include acetylene black, channel black, furnace black, lamp black and thermal black. Additionally or alternatively, the liquid-absorbent material comprises a polymer appropriate for use as a structural polymer, which is formed in a porous form using appropriate manufacturing procedures known in the art. The porous polymer may comprise a polyethylene vinyl acetate (PEVA) or a polyolefin by way of example a LDPE. Optionally, the porous polymer is formulated to have a higher melting point compared to the structural polymer used for the PCM so that the pores of the porous polymer are not substantially degraded or eliminated during incorporation into the PCM, or if the PCM is formed, for example by injection molding, into a PCWD.

A liquid-absorbent material may advantageously be included in a PCM formulation as it is capable of absorbing liquid ingredients, by way of example cannabinoids in oil dissolved in one or more carrier oils. When a cannabinoid-infused liquid-absorbent material is compounded with a structural polymer, the resulting liquid-absorbent material embedded within the structural polymer functions as a reservoir of cannabinoids. Optionally, granules of the cannabinoid-infused liquid-absorbent material is compounded into a structural polymer that has been softened with heat during manufacture of a PCM. Optionally, the PCM is a multilayered composition, comprising a cannabinoid-infused liquid-absorbent material layer and one or more structural polymer layers surrounding the liquid-absorbent material layer. Optionally, the PCM is formed to have the structural polymer layer make direct contact with the skin of the subject wearing the PCM, so that the cannabinoids infused in the liquid-absorbent material traverses the structural polymer to reach the skin of the subject. The liquid-absorbent material comprised in the PCM may be in an amount sufficient to absorb the cannabinoids and the carrier oil prior to compounding or layering with the structural polymer. By way of example, 1 gram of fumed silica may be capable of absorbing up to 10 to 20 grams of oil, while 1 gram of porous polymer may be capable of absorbing up to 3 or 4 grams of oil. Thus, the relative content of liquid-absorbent material in a PCM may depend on which porous material is used.

Optionally, the carrier oil comprises one or more non-volatile oils, which are characterized with a vapor pressure such that the oil does not substantially vaporize at about room temperature and at about standard atmospheric pressure. Optionally, the one or more non-volatile oils are (1) compatible as solvent for cannabinoids; (2) liquid at room temperature and/or body temperature and (3) compatible with topical administration on human skin. Optionally, the carrier oil comprises a paraffin oil (which may also be referred to in the art as a mineral oil) and/or one or more plant-derived oils, by way of example hempseed oil, palm oil, canola oil, linseed oil, sunflower oil, rapeseed oil, cocoa butter, olive oil, rice bran oil. Paraffin oil has been demonstrated to promote skin permeability through lipid fluidization within the outer layer of the skin (the stratum corneum) and therefore, without being bound by theory, the paraffin oil may be added in a PCM in order to enhance transdermal penetration of cannabinoids into a skin of a subject that is in contact with the PCM. The non-volatile oil may comprise between 0-40% of the total composition of the PCM. Optionally, the structural polymer and/or the non-volatile oil may include a plasticizer such as epoxidized triglyceride, by way of example epoxidized soybean oil.

Optionally, the carrier oil comprises a volatile oil, which as used herein is characterized with a vapor pressure such that the oil has a tendency to vaporize at about room temperature and at about standard atmospheric pressure. Without being bound by theory, addition of a volatile oil in a PCM formulation enhances extrusion of the cannabinoid because evaporation of the volatile oil from the surface of the PCM creates a concentration gradient that will draw more oil, together with lipophilic compounds associated with the oil, toward the surface. Optionally, the volatile oil comprises or is comprised in a natural extract or essential oil added to reduce odors associated with other active or inactive ingredients or to provide an odor generally accepted to be pleasant. A natural extract or essential may be a mixture of volatile oils and non-volatile oils. Examples of natural extracts that may be incorporated may include but are not limited to the following essential oils: Lavender oil, Valerian oil, Geranium oil, *Passiflora Edulis* Seed Oil and Chamomile oil.

Although CBD itself is less prone to oxidation than THC, in order to enhance the antioxidant properties and stability of a PCM comprising CBD or another cannabinoid, an antioxidant, for example, a phenolic antioxidant, may be added to the PCM formulation as another additive.

Optionally, a PCM comprising one or more additives may be formulated in accordance with Table 1 below.

TABLE 1

| Ingredient (Function) | Non-limiting Examples | Amount ranges (weight percent relative to total) |
|---|---|---|
| Cannabinoid (active ingredient) | CBD | 0.1-20 |
| Structural Polymer | LLDPE and LDPE | Remainder, up to 100 |
| Carrier oil | | |
| Non-volatile oil (enhances penetration of cannabinoid; control release of cannabinoid) | Paraffin Oil, plant-derived oils | 0-40 |
| Volatile Oil (Odor control/ enhances release of cannabinoid) | Plant-derived Essential oil | 0-10 |
| Liquid-absorbent material | | |
| Porous Polymer | EVA | 0-50 |
| Other liquid-absorbent material | Silica gel, fumed silica, activated charcoal | 0-5 |
| Other additives | | |
| Antioxidant | Phenolic antioxidant or butylated hydroxytoluene | 0-0.4 |
| UV stabilizer | | 0-0.4 |
| Coloring | | 0-10 |

In a more particular embodiment, PCM 20 is formulated to comprise, as weight percentages of total content: structural polymer at between 75% and 95% w/w; one or more cannabinoids at between 0.1% and 10% w/w; between 1% and 10% w/w carrier oil comprising one or more non-volatile carrier oils; and granules of a liquid-absorbent material infused with the cannabinoids and the carrier oil, the liquid-absorbent material being in an amount sufficient to absorb the cannabinoids and the carrier oil.

In an embodiment of the disclosure, the PCM is molded into a shape suitable for being worn by a subject. A PCM molded into a wearable shape is referred to herein as a plastic cannabinoid wearable device (PCWD). Optionally, a PCWD is in a shape that is wearable by a human subject or an animal subject, by way of example a necklace. Optionally, the PCWD is in a shape suitable for being worn around a neck of a subject, by way of example a necklace. Optionally, the PCWD is in a shape suitable for being worn around an arm or leg of a subject, by way of example a patch, a bracelet, a wristband, an anklet, a necklace, a collar, an armband, or a shoe insert. Optionally, the PCWD is shaped like, and functions as, a watch strap. For example, a PCWD may be used in conjunction with a usable watch worn by the subject.

PCM 20 and PCWD 10 may be produced according to the following method 100. In a block 102, the cannabinoids, optionally provided in purified form or a *cannabis* extract, are combined with a carrier oil to form a cannabinoid-infused carrier oil. In a block 104, the cannabinoid-infused carrier oil is combined with liquid-absorbent granules 25 and mixed until the cannabinoid-infused carrier oil become substantially or fully absorbed into the granules, resulting in cannabinoid-infused granules. In a block 106, the cannabinoid-infused granules are combined with components of the structural polymer, which may be in a heated environment at a temperature sufficiently high to melt the structural polymer but not the cannabinoid-infused granules 25, optionally between 110 deg. C. and 160 deg. C., to form a PCM. Optionally, the PCM is formed in a compounding extruder. In a block 108, the PCM is formed into a desired shape to form a PCWD or a component thereof. The PCM may be granulated to form PCM granules, then injection molded in a mold. Alternatively, the cannabinoid-infused granules may be mixed with structural polymer pellets during the injection molding stage. It will be appreciated that the PCM granules may be shaped into a wide variety of shapes to form different PCWDs, by way of example, wristbands (as shown in FIG. 1), anklets, patches, shoe inserts, necklaces, and the like. It will also be appreciated that the exact temperatures to which the structural polymer or PCM is heated in blocks 106 and 108 depend on the the polymers comprised in the structural polymer mix and other ingredients comprised in a given PCM.

It is well-known that many polymers, including those appropriate for use as structural polymers in PCM 20 as disclosed herein tend to be non-compatible with and resistant to oils. By way of example, laboratory or kitchen containers known in the art comprising LDPE and/or LLDPE can typically stably hold a paraffin oil or a plant-derived oil at room temperature for an extended period of time (over 30 days or more) without the oil reacting with or becoming infused into the polymer material of the container. Polyurethane and SBS rubber-based materials are also typically resistant to oils. Nevertheless, when cannabinoid-infused granules 25 were compounded with a structural polymer to create a PCM 20 formed into a PCWD 10, it was surprisingly found that the cannabinoid-infused carrier oil slowly extruded from the granules through the PCM material to form a thin layer (not shown) on an outer surface 12, 14 of the PCWD.

It was further surprisingly found that PCWD 10 being worn by a subject (not shown) in close contact to skin resulted in a slow and extended release of the cannabinoids from the PCM to the wearer of the PCWD. Without being limited by theory, being worn by the subject created a natural concentration gradient of cannabinoid-infused carrier oil between outer surface 12 of PCWD 10 and the interior of the PCWD due to transdermal absorption of the cannabinoids and carrier oil into the skin of the subject, thus driving slow release of the cannabinoid-infused carrier oil out of outer surface 12 while the PCWD was being worn. In a more particular example of a wristband-shaped PCWD 10 comprising CBD, physiological effects of low-dose CBD such as pain reduction were noted by subjects within 10 to 24 hours after wearing the wristband, and the wristbands continued to release CBD at a therapeutically effective rate even after 30 days of continuous wearing. It was also found that the PCM material remained stable and intact past 30 days of continuous wearing, and did not show any substantial signs of breakdown.

It was also surprisingly found that exemplary PCWDs did not continue to extrude the cannabinoid-infused carrier oil when the PCWD was not worn, so that as a result, the cannabinoid is not depleted when the PCWD is in storage. Similarly, outer surface 14 of the PCWD, which does not make contact with the skin of the subject when worn, did not extrude excess oil that would cause discomfort or staining. Without being bound by theory, when the PCWD is not being worn and is not in contact with an oil-absorbent surface, a thin layer of the cannabinoid-infused carrier oil that forms on the PCM surface is sufficient to negate the concentration gradient of the cannabinoid-infused carrier oil between the outer surface and the interior of PCM 20, thus preventing further extrusion of the cannabinoid-infused carrier oil to the outer surface of the PCWD.

Optionally, a PCM in accordance with an embodiment of the disclosure is for use in treating Multiple Sclerosis, Epilepsy, diabetes, or schizophrenia, anxiety, and depression. The PCM is optionally for use in lowering blood pressure. The PCM may be used for treating any condition which may benefit from the therapeutic properties of one or more cannabinoids. Optionally, the PCM is used to treat a condition causing a symptom can be alleviated with analgesic, anti-inflammatory, antineoplastic or chemo-preventive properties of CBD. Optionally, a PCM is for use in treating a human subject or an animal subject.

Exemplary, non-limiting formulations for PCWD 10 and PCM 20 are provided hereinbelow.

Example 1

An exemplary PCM comprising CBD was formulated with the following ingredients as shown in Table 2 below:

TABLE 2

| Ingredient | Percentage of total (by weight) |
|---|---|
| Structural polymer | |
| LLDPE | 20% |
| LDPE | 38.2% |
| PE elastomer | 35% |
| Cannabinoid | |
| CBD oil (20% CBD) | 1.4% (0.28% CBD) |
| Liquid-absorbent granules | |
| Porous LDPE granules | 4% |
| Fumed silica | 0.3% |
| Carrier oil | |
| Hempseed oil | 1% |
| Lavender oil | 0.1% |

The additives and the CBD oil were mixed together until the cannabinoid-infused carrier oil (the CBD oil, the hempseed oil, and the lavender oil) were absorbed into the liquid-absorbent granules (the porous LDPE granules and the fumed silica) to form cannabinoid-infused granules. The porous LDPE granules were approximately 6-10 cubic millimeters in size. The cannabinoid-infused granules were then combined with the structural polymer mixture (LLDPE, LDPE, and PE elastomer) in a compounding extruder at a temperature of between 110 degrees Celcius (deg. C.) and 130 deg. C. to form a PCM, and the PCM was then granulated to form PCM granules. The PCM granules were then injection molded into a mold in the shape of a collar to form a collar- or wristband-shaped PCWD.

Example 2

Another exemplary PCM comprising CBD was formulated with the following ingredients as shown in Table 3 below:

TABLE 3

| Ingredient | Percentage of total (by weight) |
|---|---|
| Structural polymer | |
| LDPE + PE elastomer | Remainder up to 100% |
| Cannabinoids | |
| CBD oil (40% CBD and CBDA) | 1% to 2% (0.4% to 0.8% CBD and CBDA) |

TABLE 3-continued

| Ingredient | Percentage of total (by weight) |
|---|---|
| Carrier oil | |
| Hempseed oil and paraffin oil | 3% to 5% |
| Cammomile oil | 0.1% |
| Liquid-absorbent granules | |
| Fumed silica | 0.4% to 2% (as needed to absorb carrier oil and cannabinoids) |
| Other additives | |
| Pigment | 0.5% to 1% |

The fumed silica, the CBD oil, and the carrier oils were mixed together until the oils were absorbed into the fumed silica to form cannabinoid-infused granules. The cannabinoid-infused granules were then combined with the structural polymer mixture (LLDPE, LDPE, and PE elastomer) in a compounding extruder at a temperature of between 110 degrees Celcius (deg. C.) and 130 deg. C. to form a PCM, and the PCM was then granulated to form PCM granules. The PCM granules were then injection molded into a mold in the shape of a wristband to form a wristband-shaped PCWD.

Whereas Examples 1 and 2 made use of hempseed oil or a combination of hempseed oil and paraffin oil as the carrier oil, it will be appreciated that extended release of cannabinoids from a PCM would also be achieved with other plant-derived oils such as palm oil, canola oil, linseed oil, sunflower oil, rapeseed oil, cocoa butter, olive oil, rice bran oil, with or without paraffin oil.

Whereas Examples 1 and 2 comprised CBD or CBD and CBDA in the form of CBD oil extracted from *cannabis* plants as the one or more cannabinoid, it will be appreciated that that extended release of cannabinoids from a PCM would also be achieved with (1) other cannabinoids, including other phytocannabinoids such as THC or synthetic cannabinoids that are not naturally produced in *cannabis*, provided the synthetic cannabinoid is soluble in the carrier oil; and (2) cannabinoids provided in other forms such as pure synthetic forms, by way of example dronabinol (a synthetic form of THC).

Whereas Examples 1 and 2 made use of PEs such a PE elastomer, LDPE and LLPDE, it will be appreciated that that extended release of cannabinoids from a PCM would also be achieved with other structural polymers as disclosed herein, including but not limited to a synthetic rubber or a polyurethane.

In light of the foregoing, additional exemplary PCM formulations are provided hereinbelow:

Example 3

Another exemplary PCM comprising THC is formulated with the following ingredients as shown in Table 4 below:

TABLE 4

| Ingredient | Percentage of total (by weight) |
|---|---|
| Structural polymer | |
| PE elastomer | Remainder up to 100% |
| Cannabinoids | |
| Dronabinol (100% synthetic THC) | 0.5% to 5% (depending on desired dosage) |

TABLE 4-continued

| Ingredient | Percentage of total (by weight) |
|---|---|
| Carrier oil | |
| Canola oil and cocoa butter | 0.5% to 1% |
| Liquid-absorbent granules | |
| Activated carbon | as needed to absorb carrier oil and cannabinoids |

Example 4

Another exemplary PCM comprising a wide spectrum *cannabis* extract comprising many different cannabinoids is formulated with the following ingredients as shown in Table 5 below:

TABLE 5

| Ingredient | Percentage of total (by weight) |
|---|---|
| Structural polymer | |
| LDPE + PE elastomer | Remainder up to 100% |
| Cannabinoids | |
| Wide spectrum cannabis extract (20% THC, 15% CBD, 5% CBN, 2% CBG) | 1% to 10% |
| Carrier oil | |
| paraffin oil | 3% to 5% |
| peppermint oil | 0.1% |
| Liquid-absorbent granules | |
| Fumed silica and activated carbon | as needed to absorb carrier oil and cannabinoids |

Example 5

Another exemplary PCM comprising a TPU as the structural polymer is formulated with the following ingredients as shown in Table 6 below:

TABLE 6

| Ingredient | Percentage of total (by weight) |
|---|---|
| Structural polymer | |
| TPU | Remainder up to 100% |
| Cannabinoids | |
| CBD oil (40% CBD and CBDA) | 1% to 10% (based on desired dosage) |
| Carrier oil | |
| Hempseed oil and paraffin oil | 1% to 5% |
| Chamomile oil | 0.1% |
| Liquid-absorbent granules | |
| Fumed silica | 0.5% to 6% (as needed to absorb carrier oil and cannabinoids) |

Example 6

Another exemplary PCM comprising a SBS rubber as the structural polymer is formulated with the following ingredients as shown in Table 7 below:

TABLE 7

| Ingredient | Percentage of total (by weight) |
|---|---|
| Structural polymer | |
| SBS rubber | Remainder up to 100% |
| Cannabinoids | |
| Dronabinol (100% synthetic THC) | 0.5% to 5% (based on desired dosage) |
| Carrier oil | |
| Rice bran oil and paraffin oil | 0.5% to 1% |
| Liquid-absorbent granules | |
| Fumed silica | as needed to absorb carrier oil and cannabinoids |

Example 7

Another exemplary PCM comprising a powdered CBD isolate as the cannabinoid is formulated with the following ingredients as shown in Table 8 below:

TABLE 8

| Ingredient | Percentage of total (by weight) |
|---|---|
| Structural polymer | |
| LLDPE and LDPE | Remainder up to 100% |
| Cannabinoids | |
| CBD isolate powder (over 99% pure CBD) | 0.5% to 10% (based on desired dosage) |
| Carrier oil | |
| hempseed oil and paraffin oil | 0.5% to 5% |
| Geranium oil | about 0.1% |
| Liquid-absorbent granules | |
| Carbon black | as needed to absorb carrier oil and cannabinoids |

There is therefore provided in an embodiment of the disclosure a plastic material comprising at least one cannabinoid embedded within a structural polymer, wherein the plastic material is formulated to exude the at least one cannabinoid through an outer surface of the plastic material at a therapeutically effective rate for a period of at least a week. Optionally, the plastic material is formulated to exude the at least one cannabinoid at a therapeutically effective rate for a period of at least a month. Optionally, the least one cannabinoid is exuded while the PMC remains substantially intact.

In an embodiment of the disclosure, the plastic material comprises: a liquid-absorbent material embedded within the structural polymer; and a carrier oil absorbed into the liquid-absorbent material, wherein at least one cannabinoid is dissolved in the carrier oil.

In an embodiment of the disclosure, least one cannabinoid comprises one or a combination of two or more from the group consisting of: a cannabidiol (CBD), a cannabidiolic acid (CBDA); a cannabigerol (CBG), a tetrahydrocannabinol (THC), a tetrahydrocannabinolic acid (THCA), a cannabichromene (CBC), and a cannabidivarin (CBDV).

In an embodiment of the disclosure, structural polymer comprises one or a combination of two or more of: a polyolefin, a polyvinyl chloride, a thermoplastic polyurethane, a silicone rubber, and a synthetic rubber. Optionally, the structural polymer comprises a LDPE and/or a LLDPE.

In an embodiment of the disclosure, the carrier oil is suitable for topical administration on skin of a human subject. Optionally, the carrier oil comprises a paraffin oil and/or a plant-derived oil.

In an embodiment of the disclosure, the liquid-absorbent material comprises one or a combination of two or more selected from the group consisting of: a porous polymer; a silica gel, a fumed silica, a carbon black and an activated charcoal. Optionally, the liquid-absorbent material is embedded within the structural polymer in a granular form. Optionally, the liquid-absorbent material is embedded within the structural polymer in a substantially even distribution.

In an embodiment of the disclosure, the plastic material is an adhesive material or a non-adhesive material.

There is also provided a plastic wearable apparatus comprising a plastic material in accordance with an embodiment of the disclosure, wherein the plastic material is molded into a shape suitable for being worn by a subject. Optionally, the shape is selected from the group consisting of: a patch, a bracelet, a wristband, an anklet, a necklace, a collar, an armband, and a shoe insert.

In the discussion, unless otherwise stated, adjectives such as "substantially" and "about" modifying a condition or relationship characteristic of a feature or features of an embodiment of the disclosure, are understood to mean that the condition or characteristic is defined to within tolerances that are acceptable for operation of the embodiment for an application for which the embodiment is intended. Wherever a general term in the disclosure is illustrated by reference to an example instance or a list of example instances, the instance or instances referred to, are by way of non-limiting example instances of the general term, and the general term is not intended to be limited to the specific example instance or instances referred to. Unless otherwise indicated, the word "or" in the description and claims is considered to be the inclusive "or" rather than the exclusive or, and indicates at least one of, or any combination of more than one of items it conjoins.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the disclosure in the present application are provided by way of example and are not intended to limit the scope of the disclosure. The described embodiments comprise different features, not all of which are required in all embodiments. Some embodiments utilize only some of the features or possible combinations of the features. Variations of embodiments of the disclosure that are described, and embodiments comprising different combinations of features noted in the described embodiments, will occur to persons of the art. The scope of the invention is limited only by the claims.

The invention claimed is:

1. A plastic wearable, non-adhesive device comprising a plastic material molded into a shape suitable for being worn by a subject, the plastic material comprising at least one cannabinoid embedded within a structural polymer, wherein the plastic wearable device is wristband, wherein the structural polymer comprises a low-density polyethylene (LDPE) and/or a linear low-density polyethylene (LLDPE), wherein the plastic material is formulated to exude the at least one cannabinoid through an outer surface of the plastic material at a therapeutically effective rate for a period of at least a week, wherein the plastic material comprises:
   a. a liquid-absorbent material embedded within the structural polymer; and
   b. a carrier oil absorbed into the liquid absorbent material, wherein the at least one cannabinoid is dissolved in the carrier oil.

2. The plastic wearable device according to claim 1 wherein the at least one cannabinoid comprises one or a combination of two or more selected from the group consisting of: a cannabidiol (CBD), a cannabidiolic acid (CBDA); a cannabigerol (CBG), a tetrahydrocannabinol (THC), a tetrahydrocannabinolic acid (THCA), a cannabichromene (CBC), and a cannabidivarin (CBDV).

3. The plastic wearable device according to claim 1 wherein the carrier oil comprises a paraffin oil and/or a plant-derived oil.

4. The plastic wearable device according to claim 3 wherein the carrier oil comprises hempseed oil.

5. The plastic wearable device according to claim 1 wherein the liquid-absorbent material comprises one or a combination of two or more selected from the group consisting of: a porous polymer; a silica gel, a fumed silica, a carbon black and an activated charcoal.

6. The plastic wearable device according to claim 5 wherein the liquid-absorbent material is fumed silica.

7. The plastic wearable device according to claim 1 wherein the initial total weight of cannabinoid in the plastic material is between 0.1% and 15% of the weight of the plastic material.

8. The plastic wearable device according to claim 7 wherein the initial total weight of cannabinoid in the plastic material is between 0.5% and 2.5% of the weight of the plastic material.

9. The plastic wearable device according to claim 1 wherein the initial total weight of carrier oil in the plastic material is between 0.1% and 10% of the weight of the plastic material.

10. The plastic wearable device according to claim 3 wherein the initial total weight of carrier oil in the plastic material is between 1% and 10% of the weight of the plastic material.

11. The plastic wearable device according to claim 3 wherein the initial total weight of carrier oil in the plastic material is between 1% and 2% of the weight of the plastic material.

12. The plastic wearable device according to claim 1 wherein the liquid-absorbent material is embedded within the structural polymer in a granular form.

13. The plastic wearable device according to claim 1, wherein when the device is worn by the subject, does not adhere to the skin of the subject.

14. The plastic wearable device according to claim 2 wherein the cannabinoid is selected from the group consisting of CBD and CBDA.

15. The plastic wearable device according to claim 14 wherein the amount of cannabinoid is between 0.5% and 2.5%.

16. The plastic wearable device according to claim 1, wherein the initial weight of structural polymer in the plastic material is between 75% and 95%.

17. A method for administering cannabinoid to a subject comprising wearing the plastic wearable device according to claim 1.

* * * * *